United States Patent [19]

Hill et al.

[11] Patent Number: 5,032,387
[45] Date of Patent: Jul. 16, 1991

[54] DENTAL AND ORAL HYGIENE PREPARATIONS

[75] Inventors: Ira D. Hill, Locust; Robert D. White, Midland Park, both of N.J.

[73] Assignee: Princeton Pharmaceutical Inc., Paterson, N.J.

[21] Appl. No.: 927,752

[22] Filed: Nov. 6, 1986

[51] Int. Cl.$^5$ .............................................. A61K 7/16
[52] U.S. Cl. ................................. 424/49; 424/56; 222/402.1; 222/402.12; 222/424.5; 239/350; 514/901
[58] Field of Search ................ 424/49, 56, 439; 514/901; 239/350; 222/424.5, 402.1, 402.12

[56] References Cited

U.S. PATENT DOCUMENTS

| | | | |
|---|---|---|---|
| 1,411,681 | 4/1922 | Burlew | 424/49 |
| 1,633,336 | 6/1927 | Larson | 424/49 |
| 2,004,957 | 6/1935 | Messner | 424/455 |
| 2,024,146 | 12/1935 | Crowther | 424/49 |
| 2,031,233 | 2/1936 | Stillwell | 424/451 |
| 2,089,845 | 8/1937 | Atkins | 424/49 |
| 2,677,700 | 5/1954 | Jackson et al. | 568/618 |
| 2,778,045 | 1/1957 | Bly et al. | 15/198 |
| 3,228,845 | 1/1966 | Najjar | 424/49 |
| 3,431,339 | 4/1969 | Gyarmathy et al. | 424/52 |
| 3,475,533 | 10/1969 | May | 424/57 |
| 3,574,824 | 4/1971 | Echeandia et al. | 424/50 |
| 3,639,563 | 1/1972 | Januszewski | 424/49 |
| 3,907,991 | 9/1975 | Accetta | 424/49 |
| 3,929,988 | 12/1975 | Barth | 424/54 |
| 3,947,570 | 3/1976 | Pensak | 424/54 |
| 3,957,964 | 5/1976 | Grimm III | 424/10 |
| 4,011,309 | 3/1977 | Lutz | 424/49 |
| 4,069,312 | 1/1978 | Mannara | 424/49 |
| 4,071,614 | 1/1978 | Grimm III | 424/49 |
| 4,130,636 | 12/1978 | Tomlinson | 424/52 |
| 4,143,126 | 3/1979 | Gaffar | 424/49 |
| 4,343,785 | 8/1982 | Schmolka | 424/49 |
| 4,420,472 | 12/1983 | Boden | 424/58 |
| 4,446,157 | 5/1984 | Boden | 426/3 |
| 4,465,661 | 8/1984 | Schmolka | 424/49 |
| 4,465,663 | 8/1984 | Schmolka | 424/62 |
| 4,476,107 | 10/1984 | Schmolka | 424/49 |
| 4,511,563 | 4/1985 | Schmolka | 514/162 |

FOREIGN PATENT DOCUMENTS 0075410 4/1985 Japan.

OTHER PUBLICATIONS

The Merck Index, 9th ed., Merck & Co., Inc., Rahway, N.J., 1976, Citations 6971 and 7349.
Afseth, Caries. Res., 17: 472–475 (1983).
Bowden, Can. Dent. Assoc. J. 50, p. 169 (1984).
Harrap et al., Archs. Oral Biol., vol. 29, No. 2, pp. 87–91 (1984).
Harrap et al., Journal of Peridontal Research, 18: 634–642 (1983).
Havenaar, J. Dent. Res., vol. 63, No. 2, 120–123 (1984).
Hayes, J. Dent. Res., vol. 63, No. 1, 1–5 (1984).
Jari, Advances in Pharmacology and Chemotherapy, vol. 20, 191–218 (1984).
Loesche et al., Jada, vol. 108, 587–592 (1984).
Makkinen et al., Jada, vol. 111, 745–751 (1985).
Mordenti et al., Journal of Pharmaceutical Sciences, vol. 71, No. 12, 1410–1421 (1982).
Segal et al., Journal of Pharmaceutical Sciences, vol. 74, No. 1, 79–81 (1985).
Southard et al., Jada, vol. 108, 337–441 (1984).
Topitsglou et al., Caries. Res. 17: 369–378 (1983).
Winter et al., Caries. Res. 16: 349–352 (1982).
Jada, vol. 109, 690–702 (1984).
Fine et al., Journal of Clinical Periodontology, 12: 660–666 (1985).
van Houton, et al., Rev. Infect. Dis., vol. 5, Suppl. 4, pp. 5659–5669 (1983).
van Houton et al., J. Infection 10, (4) 252–260 (1982).

*Primary Examiner*—Ronald W. Griffin
*Attorney, Agent, or Firm*—Ernest V. Linek

[57] ABSTRACT

Disclosed is an oral hygiene preparation in the form of a dentifrice spray comprising a portable pump containing a dental cleansing/coating composition suitable for frequently dispensing premeasured dosages to clean the mouth, interrupt plaque formation and provide a prolonged clean, just-brushed feeling.

19 Claims, No Drawings

DENTAL AND ORAL HYGIENE PREPARATIONS

BACKGROUND OF THE INVENTION

The present invention relates to oral hygiene and specifically to the frequent cleansing of the oral cavity and interference with the formation of plaque. Plaque is a microbial coating on tooth surfaces, bound together by natural polymers, (mucopolysaccharides,) formed by microbial action on the cell debris, food remnants, sugars and starches in the mouth. Embedded in this polymer matrix are the bacteria normal to the oral cavity but, when trapped against tooth surfaces and protected by the matrix from easy removal, are in excellent position for "mischief." Most dental texts implicate plaque in the formation of caries, or tooth decay. In addition, these embedded bacteria release toxins that cause gingivitis, bleeding and swelling of the gums. Gingivitis can lead to periodontitis in which gums recede, pockets of infection form and teeth loosen.

Plaque formation is an ongoing process. Various gel and paste dentifrice preparations, mouth rinse and mouth prerinse preparations make plaque and/or tartar control claims. One disadvantage of these preparations is that only a relatively short time during which the teeth are being cleaned or the mouth is being rinsed is available for these preparations to take effect. These preparations generally have little residual effect on plaque formation. Additionally, some of these preparations such as mouth rinses and prerinses contain various antimicrobial substances which may alter the critically balanced microflora of the mouth. Another disadvantage of these preparations is the general infrequency of use. That is, most are used once or perhaps twice daily and seldom when they are most needed, e.g., after meals, snacks, smoking, drinking, coffeebreaks, etc.

Effective oral hygiene requires that three control elements be maintained by the individual:

1. Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.

2. Surfactant Cleansing. This is required to remove: food debris and staining substances before they adhere to the tooth surfaces; normal dead cellular (epithelial) material which is continually sloughed off from the surfaces of the oral cavity and microbial degradation products derived from all of the above. Besides the obvious hygenic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.

3. Frequency of Cleansing. This is perhaps the most difficult to provide in today's fast-paced work and social environment. Most people recognize that their teeth should be brushed at least 3 times a day plus after each snacking occasion.

The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Thus, the 24 hour period between brushings for a majority of the population provides optimum plaque forming conditions with no interruptions.

Since plaque is regarded by most of the dental profession as a causitive agent leading to various dental pathologies as noted above, there is considerable desire by most consumers to remove or prevent the formation of plaque on a daily basis. There are three oral care strategies which address the problem of plaque: abrasion, anti-microbial agents and removal of precursors to plaque.

1. Abrasive removal of the plaque film, once it has firmly adhered to the tooth surface, is the only totally effective cleansing mechanism. Again, professional dental hygiene is the most effective, but recently a number of special abrasive toothpastes have been accepted by dental organizations as partially removing adhered plaque and the tartar which subsequently forms from the plaque.

2. Antimicrobial action could affect plaque formation in two ways, (a) reducing the number of bacteria in the mouth which form the mucopoly-saccharides and (b) killing those bacteria trapped in the film to prevent further growth and metabolism. However, the medical and dental community is divided about the advisability of frequent use of antimicrobial agents in the mouth in rinses or prerinses, especially the most effective ones, except under strict supervision of licensed practitioners. There are a number of reasons given, but one concern is that such materials would upset the ecological balance of the mouth. A balanced, "friendly" microbial population is necessary to prevent pathogenic organisms from taking over.

3. Removal of plaque precursors requires the reduction of food sources and building blocks required for the bacteria to synthesize the mucopolysaccharides which polymerize into the plaque film. Going far back into the chain of events leading to plaque formation and interrupting the chain has much to commend it as a sound oral hygiene strategy. However, for this strategy to be effective, the plaque building blocks must be interrupted periodically. As noted above, hereto, the oral hygiene preparations described about fall short on "frequency-of-use" basis.

For reference, see, L. Menaker, *The Biologic Basis of Dental Caries,* Chapters 5, 11, 12, 14 16 and 18, Harper & Row (1980).

SUMMARY OF THE INVENTION

It has now been found that plaque formation can be disrupted by periodically spraying premeasured dosages of the compositions of this invention into the mouth. This interference with the plaque forming process is carried out without substantially altering the critically balanced microflora of the mouth. The compositions of the present invention contain a combination of cleaning and coating substances in a sprayable liquid dentifrice that leaves the mouth with a prolonged clean, just-brushed feeling.

The present invention combines two of the three primary elements of oral hygiene, namely surfactant cleansing and frequent cleansing. The latter element is especially important in that it is the product difference which no previous oral hygiene product has successfully implemented. Plaque fighting of the present invention is based on a unique novel interruption theory conveniently reduced to practice, i.e., the disruption of plaque formation without resort to antimicrobial ingredients. This interruption of plaque formation is further enhanced by the presence of a smooth, thin film of coating substance in the oral cavity which makes it more difficult for plaque to attach to the teeth. The present invention represents the next major advance in oral hygiene after regular brushing with an abrasive dentifrice paste/or rinsing with various plaque fighting rinses and prerinses.

DETAILED DESCRIPTION OF THE PREFERRED EMBODIMENT

The present invention comprises:

I. a portable container, suitable for pocket or purse, provided with a metered pump, wherein, the container can be conveniently carried and used frequently throughout the day, particularly after meals, snacks, drinks, coffee breaks and smoking; to dispense a pre-measured dosage of the composition of the invention, and II. a sprayable liquid dentifrice containing a combination of cleaners and coating substances wherein:

a. the cleaners include: surfactants and emulsifiers such as:
  sodium lauryl sulfate,
  sodium lauroyl sarcosinate,
  polyethyleneglycol stearate,
  polyethyleneglycol monostearate,
  coconut monoglyceride sulfonates,
  soap powder,
  sodium alkyl sulfates,
  sodium alkyl sulfoacetates,
  alkyl polyglycol ether carboxylates such as those described in U.S. Pat. No. 4,130,636 polyoxyethylene derivatives or sorbitan esters, such as those described in U.S. Pat. Nos. 3,639,563; 3,947,570,
  propoxylated cetyl alcohol as described in U.S. Pat. No. 2,677,700; and Preferred commercially available substances which include:
  polyoxyethylene - polyoxybutylene block
  copolymers such as Pluronic F108, and F127 (BASF) and polysorbates such as Tween 40, and 80, (Hercules).

Particularly preferred surfactants include block copolymers comprising a cogeneric mixture of conjugated polyoxybutylene and polyoxyethylene compounds having as a hydrophobe, a polyoxybutylene polymer of at least 1200 molecular weight; such as described in U.S. Pat. Nos. 4,343,785, 4,465,663; 4,511,563 and 4,476,107, and b. the coating substances can be characterized as follows, they:
(1) suppress the tendency of the surfactant cleaners present to foam,
(2) are safely ingestible at the concentrations used,
(3) have an affinity for mouth and teeth surfaces,
(4) are neutral, inert and do not support biological activity,
(5) modify the surface energy properties of surfaces of the mouth such that it is more difficult for food particles, cellular debris and various plaque precursors and formers to attach to these surfaces,
(6) form a thin, transparent coating that does not build up on mouth surfaces and is removed by the normal clearing and flushing action of the mouth,
(7) impart a pleasant "smooth" feeling to the surfaces of the mouth and teeth, and
(8) retain various flavors and substances on surfaces of the mouth imparting an unexpected prolonged flavor effect.

(c) the coating substances include: various silicones, long chain hydrocarbons, carbowaxes and polymers such as:
  silicone glycol co-polymers,
  polydimethyl siloxanes,
  long chain hydrocarbons, especially normal paraffins having a chain length of 16 carbon atoms or greater, paraffins with several loci of branching and unsaturation, where the extend of such branching and unsaturation does not create unacceptable toxicity nor lower the solidification point below body temperature, Carbowaxes ® (polyethylene glycols), and polymers which have limited solubility in ethanol and water solutions where the ethanol: water ratio is greater than 0.3:1 but have essentially no solubility in water or saliva at lower ratios.

The combination of certain cleaners with certain coating substances, wherein the latter is inherently insoluble in the former, in a dentifrice spray is novel. The results obtained with a dentifrice spray containing this combination in the mouth, is novel. Furthermore, the cleaner/coating substance/saliva mixture obtained in the mouth is ingestible and can be pleasantly swallowed, which further distinguishes it from typical dentrifices used with a toothbrush and most rinses and prerinses. For example, unlike typical cleaners used in dentifrice pastes, the cleaners of the present invention do not fill the mouth with foam and can be pleasantly swallowed which is necessary for the high frequency cleaning feature of the present invention.

Surprisingly, the cleaning/coating combination of the present invention retains good surface active properties and is able to clear the mouth of some cell debris, food debris, material alba, sugars, starches and other precursors to plaque. This cleaning is obtained with minimal foaming while simultaneously coating the surfaces of the oral cavity with a thin neutral film containing the flavorants of the composition. This neutral film is not metabolizable by resident oral cavity microorganisms.

By contrast, natural film formers such as lecithin-containing substances and fats are known to form antiattachment films on mouth surfaces but these films are not suitable for the purposes of the present invention since they are metabolizable and are not neutral. Most of these naturally occurring coating substances support biological activity rather than form non-supportive inert films and as such, work opposite of the suitable film formers of the present invention. See for example; Menaker, *The Bioloqic Basis of Dental Caries*, Chapter 16; Gibbons and Hoote, *Ann. Rev. of Microbiol*, 29 pp. 19-44; and Hayes, *J. Dent. Res.*, 632, pp. 2-5 (1984)

As long as this transient inert coating remains, it:
1. restricts the subsequent adherence of plaque forming materials to the teeth, thus continuing the disruption of plaque formation;
2. continues to impart a "smooth" feeling to the mouth, and
3. prolongs the flavor perception of the dentifrice spray.

These features are described in Examples 1-6 below. The prolonged flavor perception, described as a "clean, just-brushed feeling," is particularly novel and unexpected.

Most users of the present invention perceive a quite different feeling in the mouth than is perceived with typical dentifrice pastes and/or gels. For example, (1) the mouth feels exceptionally clean and smooth and the surfaces of the teeth are slick and shiny. This well lubricated feeling of the mouth is particularly beneficial to mouth breathers and those afflicted with mouth dryness. (2) the prolonged flavor perception is generally described as "freshness" and persists much longer with the compositions of the present invention than when the same flavor is introduced into the mouth in the form of a breath freshener, mint, gum or in a traditional dentifrice and/or mouth rinse or prerinse. This residual flavor benefit is an important element contributing to frequency of use, and (3) prior to swallowing the cleaner/coating/saliva mixture, the user perceives that the combination is "doing something" in the mouth. This perceived signal of efficacy reinforces repeat usage and often motivates the user to frequent use; a key element is maximizing the efficacy of the present invention.

Combining the various cleaning/coating/mouth-feeling benefits of the compositions of the invention with a portable delivery system, for example, a small pump spray, provides for the first time, a commercializeable product whose form of delivery works in conjunction with the product to be dispensed to promote frequent use i.e., frequent cleansing. As noted above, infrequent cleansing remains as the major road block to effective oral hygiene. Effective but socially inconvenient toothpaste, mouth rinses, and prerinses are simply not used with the frequency required to obtain optimum interruption of plaque formation.

Portable delivery systems suitable for the present invention include: drops dispensesed from an eye-dropper type dispenser, masticatable capsules, liquid center chewing gums and the like.

The portable delivery system preferred for the present invention includes a plastic, metal or glass container fitted with a dispensing means, such as a valve, pump, etc. Preferred embodiments include metered pump sprays or a metered aerosol valve embodiment includes metered pump sprays or a metered aerosol valve system. In a particularly preferred embodiment of the invention, the container is made of a clear plastic such as molded oriented polyethylene terephthalate (PET), with a capacity between about 0.2 and about 0.5 fluid ounces, and is fitted with a 13 mm pump spray. A particularly preferred embodiment includes a clear, PET, 0.35 fluid once container with a 13 mm neck finish, fitted with a metered pump spray that dispenses between 100 and 120 metered sprays. Preferably, the dispensing system delivers between 0.002 and about 0.005 ounces per measured spray. Preferably the individual dosages dispenses are in the form of a tight spray pattern that can be targeted towards the tip of the tongue.

Frequency of cleansing is encouraged by two unique characteristics of the present invention. These cause the user to return to the invention frequently throughout the day, stimulated as much by enjoyment, as by conscious recall of "my mouth needs cleaning" after events such as meals, snacks, coffee breaks, drinks, smokes, etc. These characteristics are:

a. The preferred package is convenient to use. The preferred pump spray container, for example, easily slips into the pocket or purse, encouraging the product to be close at hand in any work or social environment. Delivery of an effective quantity is simple, quick and discrete.

b. The product is pleasant to use. The various flavors in the compositions of the present invention are formulated to be as pleasant as a good quality mint and to contribute this pleasant taste over a longer-than- expected time period thus enhancing the "its working" perception without negative medicinal connotations which are found to reduce frequency of use and undermine the frequent cleansing advantage. The feeling in the mouth is equally pleasant. A smooth, tingly "something's happening" feeling is perceived immediately upon application, followed by a clean, fresh, well lubricated mouth and tooth surface which unexpectedly persists much longer than mints, gums, breath fresheners and even mouth washes and toothpastes.

Research shows that it is not unreasonable for a typical user of the instant dentifrice spray to use about 0.2 ounces/week from a dispenser that delivers approximately 0.0035 ounces per depression of the pump. Approximately three 0.35 ounce containers are used by a typical user in a 30 day period.

The compositions of the present invention may also contain a fluorine-containing compound which has a beneficial effect on the care and hygiene of the oral cavity, such as sodium fluoride or stannous fluoride in an amount up to one percent, preferably between 0.1 percent by weight and one percent by weight of the dentifrice spray, based on the water soluble fluorine content thereof.

The compositions of the invention may also contain certain phosphate salts, such as sodium pyrophosphate, which have been shown to aid in the control of plaque and the calcified plaque called tartar.

The high flavor levels which can be pleasantly incorporated into this invention, whose frequent application is encouraged by the unique character of the invention, and which are retained in the mouth for surprisingly long time periods as discussed below in Examples 1–6 also contribute to the plaque controlling properties of this invention. For example, natural and synthetic flavor and sweetner agents as diverse as menthol, xylitol and glycyrrhizin are known to be beneficial towards plaque control and are included in the compositions of this invention (Reference: Segal, *J. Pharm. Sci.*, 74 pp. 79–81 (1985) and Makkinen, *J. Am. Dent. Assoc. III*, pp. 740–741).

In addition to the cleaning/coating compositions described above, preferred embodiments of the present invention use various viscosity control agents to impart certain viscosity characteristics to the products of the invention. It is believed that in these preferred embodiments of the invention, viscosity plays a role in achieving optimum mouth feel and flavor retention characteristics of the invention.

Viscosity between about 30 and about 600 cps is preferred and between about 70 and 250 cps is particularly preferred. Viscosity control agents are known in the prior art and can be selected from natural and synthetic gums such as gum tragacanth, methyl cellulose, polyvinyl pyrrolidone, and hydrophylic carboxyvinyl polymers such as those sold under the trademark Carbopol 934. Generally, about 0.1 percent to about 5 percent of a solution of viscosity control agent is used. See Table I.

Alcohol, flavors, colorants, sweetners, zylitol and humectants are also used to impart optimum cosmetic characteristics to the compositions of the present invention.

Generally, the flavoring component is present as a denaturant in the non-toxic alcohol component, i.e., ethyl alcohol. The conventional flavoring components are exemplified by the following materials, menthol, anise oil, benzaldehyde, bitter almond oil, camphor, cedar leaf oil, cinnamic aldehyde, cinnamon oil, citronella oil, clove oil, eucalyptol, heliotropine, lavendar oil, mustard oil, peppermint oil, phenyl salicylate, pine oil, pine needle oil, rosemark oil, sassafras oil, spearmint oil, thyme oil, thymol, wintergreen oil, lemon and orange oils, vanillin, and other flavoring oils generally regarded a safe (GRAS) by health authorities.

The compositions of the present invention generally contain about 30 to 65 percent, preferably about 40 to 50 percent by weight of water and from 30 to about 60 preferably about 40 to 55 percent by weight, most preferably about 45 percent by weight of a non-toxic alcohol such as ethanol. See Tables I and II. All percentages referenced in Tables I and II are percent by weight.

Additional adjuvants can be added to provide color, flavor, or sweetening effects, as desired. Examples of suitable sweetening agents include sorbitol, sodium cyclamate, saccharine, commercial materials such as Nutrasweet® brand of aspartame and xylitol. The coloring agent is typically added in an amount of 0.01 percent to about 0.02 percent by weight. Citric acid is often utilized as a flavor additive. All types of flavoring materials are generally used in amounts of about 0.01 to about 5.0 percent by weight, preferably about 0.05 percent to about 3.0 percent by weight. (See Table I).

A buffering ingredient may also be added to the compositions of the invention in order to prevent natural degradation of the flavoring components. Generally, the pH of these compositions is adjusted to 3.5 to about 7, preferably from about 5 to about 6. The buffering ingredients such as an alkali metal salt of a weak organic acid, for instance, sodium benzoate, sodium citrate, sodium phosphate, or potassium tartrate is generally added in an amount of about 0.1 to about 1.0 percent by weight.

In addition to the water, alcohol, flavoring and pH buffering ingredients, the compositions of the invention can optionally contain at least one humectant selected from the group consisting of glycerine, xylitol, sorbitol and propylene glycol. Generally, such humectants are utilized in the proportion of about 3 percent to about 12 percent by weight based upon the total weight of the composition. Preferably, the humectant is utilized in an amount of about 3 to 4 percent by weight (See Table I).

The spray pattern of the compositions of the present invention can be adjusted to optimize the perceived benefits of mouth, feel, etc. For example, an aerosol spray tends to be more broken up and discharged with greater force than that obtained with a pump spray. In certain preparations of the present invention, the aerosol spray is overwhelming and not a pleasant experience. The ideal spray pattern is obtained with a pump spray wherein the exit orifice of the actuator is such that a tight pattern of spray is obtained on the tongue when the pump spray is activated 2 to 4 inches from the tongue. The organoleptic properties of the compositions of the present invention are generally such that the user who receives such a tight spray pattern on the tongue naturally tends to immediately rub the tongue over the surfaces of the mouth which assists deployment of the cleaning/coating composition and imparting the prolonged mouth feel.

EXAMPLES

The following examples provide a synopsis of dental and oral hygiene preparations combined according to the invention in metered pump sprays and show the unexpected results obtained by the use of the compositions disclosed herein. The examples are intended for the purpose of illustration and are not to be construed as limiting in any way.

The water used was deionized. The various ingredients were mixed using standard blending practices. The various samples were packaged in clear 0.35 fluid ounce PET containers fitted with 13 mm metered pumps having a discharge capacity of between 100 and 120 metered sprays/ 0.35 fluid ounces of the composition of the invention. The standard use rate is 3 metered sprays per use. The viscosity of these various preparations ranged from between about 30 and about 300 centipoises.

The spray pattern was tight and most consumers sprayed the various preparations onto the tongue from one to four inches away. Most used two or three premeasured sprays per use. The compositions of the invention were usually sprayed onto the tongue, rubbed over the teeth and mouth surfaces and not expectorated. In Table I the percent by weight of each component is listed immediately after the component.

TABLE I (PERCENT BY WEIGHT)

| Example | Cleaner(s) | Coating Substance | Thickener | Polyol(s) | Sweetner(s) | Flavor | Colorant | Water | Alcohol | Total % by Wt |
|---|---|---|---|---|---|---|---|---|---|---|
| 1 | Pluronic F-127 0.4 | Silicone A-F Emulsion (Dow Corning) 0.03 | Methocel K-4M 0.3 | Sorbital (70% Soln) 8.5 Glycerine 3.0 | Sodium Saccharin 0.65 | IFF Vanilla Mint #101 1.0 | FD&C Red #33 (17% Soln) 0.4 | 41.36 | 43.86 | 100 |
| 1a | same as 1 | none | same as 1 | same as 1 | same as 1 | same as 1 | same as 1 | 41.39 | 43.86 | 100 |
| 2 | same as 1 | Silicone A-F (Dow Corning) Emulsion 0.02 | same as 1 same as 1 | same as 1 same as 1 | same as 1 same as 1 | same as 1 same as 1 | same as 1 same as 1 | 41.37 | 43.86 | 100 |
| 3 | same as 1 | Silicone A-F (Dow Corning) Emulsion 0.06 | same as 1 same as 1 | same as 1 same as 1 | same as 1 same as 1 | same as 1 same as 1 | same as 1 same as 1 | 41.37 | 43.86 | 100 |
| 4 | Sodium Lauryl Sulfate 1.5 | Silicone 190 NFF (Dow Corning) 2.5 | Methocel K-4M (29% Soln) 5.0 | Glycerine 10.0 | Sodium Saccharin 0.6 Honey | Spearmint Oil 0.25 Peppermint Oil | FD&C Red #33 (0.5% | 9.95 | 54.45 | 100 |

TABLE I-continued (PERCENT BY WEIGHT)

| Example | Cleaner(s) | Coating Substance | Thickener | Polyol(s) | Sweetner(s) | Flavor | Colorant | Water | Alcohol | Total % by Wt |
|---|---|---|---|---|---|---|---|---|---|---|
| | | | | 13.5 | | 0.25 | Soln) 2.0 | | | |
| 5 | Sodium Lauroyl Sarcosinate 0.25 PEG 0.08 | Silicone A-F (Dow Corning) Emulsion 0.01 | Methocel K-4M 0.25 | Glycerine 3.5 | Sodium Saccharin 0.5 | IFF Citrus Mint #099 1.0 | None | 47.0 | 47.31 | 100 |
| 6 | Carbowax 4000 0.1 Tween 40 0.5 | Silicone A—F Emulsion (Dow Corning) 0.01 | Methocel K-4M 0.3 | Glycerine 3.0 Sorbitol (anhydrous) 6.0 | Sodium Saccharin 0.3 | IFF Spice Mint #098 0.5 | None | 44.0 | 45.29 | 100 |

DISCUSSION OF EXAMPLES 1 TO 6

Example 1

When evaluated by six people experienced in oral care products, this composition was found to clean the mouth quickly of food debris and left the mouth well lubricated and the teeth feeling smooth and shiny. Surprisingly, when evaluated by two very experienced flavor evaluators, a clearly definable taste, characteristic of the flavor included, could be perceived for 30 minutes while some less specific flavor/freshness perceptions persisted up to 65 minutes. The same flavor concentrations in ethanol/water/saccharin solutions were perceived as a clearly definable taste characteristic for only 10 minutes after being sprayed in the mouth while some less specific flavor/freshness percentions persisted for about 20 minutes. These latter results would be expected by one skilled in the art, but not the former which are surprisingly long lasting.

Example 1a: was found to be very foamy in the mouth and unpleasant to swallow. The mouth does not feel as smooth nor are the teeth perceived as clean and shiny. Immediately upon swallowing, the mouth feels dry.

Example 2

The composition was perceived similar to Example 1 except that the residual "mouth feel" was less pronounced and the immediate feeling upon application was a little more "whipped cream" like. The lasting of flavor perception was not measured.

Example 3

The mouth coating was very pronounced. Some evaluators found the mouth coating effect very pleasant while others perceived the mouth to be artificially lubricated.

Example 4

A distinctly different mouth feel was perceived that was different from previous examples. Good mouth cleaning was observed with a slight detectable foaming. The clean shiny feeling was less pronounced.

Example 5

A good mouth cleaning action was perceived. A heavier feeling after swallowing was noted. The teeth feel was moderately smooth and shiny. Flavor response on impact was good. Residual flavor effect was not tested.

Example 6

A good mouth cleaning action was perceived and a more slick feeling on the tongue than in Example 1. The tooth surface feeling was good.

Various combinations of cleaners and coating substances of the invention in a range of concentrations are set out in Table II below.

TABLE II

| Example | Cleaner | Concentration | Coating Substance | Conc. |
|---|---|---|---|---|
| 7 | sodium lauryl sulfate | 0.05 | Dow Corning Silicone AF emulsion | .005 |
| 8 | Pluronic 127 | 3.0 | Dow Corning Silicone AF emulsion | .3 |
| 9 | sodium lauroyl sarcosinate | 0.1 | Dow Corning Silicone AF emulsion | 0.01 |
| 10 | sodium lauryl sulfate | 1.5 | Dow Corning Silicone AF emulsion | 0.1 |
| 11 | Pluronic F-127 | 0.2 | Dow Corning Silicone AF emulsion | 0.02 |
| 12 | sodium lauroyl sarcosinate | 0.8 | Dow Corning Silicone AF emulsion | 0.06 |
| 13 | sodium lauryl sulfate | 0.2 | Silicone glycol copolymer Dow Corning #190Nff | .5 |
| 14 | Pluronic F-127 | 0.3 | Silicone glycol copolymer Dow Corning #190Nff | 5.0 |
| 15 | sodium lauroyl sarcosinate | 0.4 | Silicone glycol copolymer Dow Corning #190Nff | 1.5 |
| 16 | sodium lauryl sulfate | 0.5 | Silicone glycol copolymer Dow Corning #190Nff | 3.0 |
| 17 | Pluronic F-127 | 0.6 | propylene glycol monostearate (Mazol PGMS) | 0.001 |
| 18 | sodium lauroyl sarcosinate | 0.7 | propylene glycol monostearate (Mazol PGMS) | 0.5 |
| 19 | sodium lauryl sulfate | 0.8 | polyethylene glycol stearate (MAPEG S-40-K) | 0.01 |
| 20 | Pluronic F-127 | 0.9 | polyethylene glycol stearate (MAPEG S-40-K) | 0.2 |
| 21 | sodium lauryl sarcosinate | 1.0 | polyethlene glycol (carbowax) | 0.05 |
| 22 | sodium lauryl sulfate | 1.1 | polyethlene glycol (carbowax) | 0.1 |

While this invention has been described with reference to certain preferred embodiments, it will be recognized by those skilled in the art that many variations are possible without departing from the scope and spirit of the invention and it will be understood that it is intended to cover all changes and modifications of the invention disclosed herein for the purpose of illustration which do not constitute departures from the spirit and scope of the invention.

What is claimed is:

1. An ingestible, nonfoaming, oral hygiene preparation that coats mouth surfaces with a plaque matrix disrupting film, said preparation consisting essentially of:
   (a) an ingestible surfactant selected from the group consisting of:
      sodium lauryl sulfate,
      sodium lauryl sarcosinate,
      polyethylene glycol stearate,
      polyethylene glycol monostearate,
      coconut monoglyceride sulfonates,
      block copolymers of polyoxyethylene and polyoxybutylene,
      alklypolyglycol ether carboxylates,
      polyethylene derivatives of sorbitan esters,
      propoxylated cetyl alcohol,
      block copolymers comprising a cogeneric mixture of conjugated polyoxybutylene and polyoxylethylene compounds having as a hydrophobe a polyoxybutylene polymer of at least 1200 molecular weight,
      a salt of a fatty acid (soap, powder, and mixtures thereof, and
   (b) an ingestible coating substance, insoluble in said surfactant, selected from the group consisting of:
      silicones,
      silicone glycol copolymers,
      polydimethyl siloxanes,
      normal paraffins having a chain length of at least 16 carbon atoms,
      paraffins with several loci of branching and unsaturation,
      carbowaxes,
      polymers with a limited solubility in ethanol and water solutions where the ethanol:water ratio is greater than 0.3:1 but having essentially no solubility in water or saliva at lower concentrations,
   and mixtures thereof:

2. An ingestible, nonfoaming oral hygiene preparation of the composition in claim 1 in the form of a dentrifice spray comprising a portable pump containing a dental cleansing and coating composition suitable for frequently dispensing premeasured dosages of said composition sufficient to clean the mouth, interrupt the formation of plaque and provide a prolonged flavor.

3. The ingestible, nonfoaming oral hygiene composition of claim 1 suitable for interrupting the formation of plaque consisting essentially of a mixture of alcohol, water, surfactant, coating composition, flavor, humectant, thickener, colorant, and sweetener contained in a portable container fitted with a dispensing means, said oral hygiene composition being insoluble in said surfactant.

4. The ingestible, nonfoaming oral hygiene composition of claim 1 suitable for producing a prolonged flavor effect in the mouth consisting essentially of a surfactant, coating, alcohol, water mixture containing from between about 0.1 and about 2.0 percent by weight flavorant.

5. The ingestible, nonfoaming oral hygiene composition of claim 1 suitable for interrupting the formation of plaque on tooth surfaces, consisting essentially of a mixture of alcohol, water, surfactant, silicone and flavorant, dispensable via a metered spray.

6. The oral hygiene composition of claim 5 wherein the surfactant is a polyoxyethylene-polyoxybutylene block copolymer.

7. The oral hygiene composition of claim 5 wherein the surfactant is sodium lauryl sulfate.

8. The oral hygiene composition of claim 5 wherein the surfactant is a mixture of sodium lauroyl sarcosinate and polyethylene glycol stearate.

9. The oral hygiene composition of claim 5 wherein the surfactant is a polydimethyl siloxane or a food and drug suitable emulsion thereof.

10. An ingestible, nonfoaming, oral hygiene preparation, having a viscosity between about 30 and about 600 centipoises, suitable for coating mouth surfaces with a plaque matrix, disrupting film, said preparation consisting essentially of
   (a) from between about 0.05 and about 3.0 percent by weight of an ingestible surfactant selected from the group consisting of:
      sodium lauryl sulfate,
      sodium lauryl sarcosinate,
      polyethylene glycol stearate,
      polyethylene glycol monostearate,
      coconut monoglyceride sulfonates,
      sodium block copolymers of polyoxyethylene and polyoxybutylene,
      alkylpolyglycol ether carboxylates,
      polyethylene derivatives of sorbitan esters,
      propoxylated cetyl alcohol,
      block copolymers comprising a cogeneric mixture of conjugated polyoxybutylene and polyoxylethylene compounds having as a hydrophobe a polyoxybutylene polymer of at least 1200 molecular weight,
      a salt of a fatty acid, and
      mixtures thereof, and
   (b) an ingestible coating substance, insoluble in said surfactant, selected from the group consisting of:
      silicones,
      silicone glycol copolymers,
      polydimethyl siloxanes,
      normal paraffins having a chain length of at least 16 carbon atoms,
      paraffins with several loci of branching and unsaturation,
      carbowaxes,
      polymers with a limited solubility in ethanol and water solutions where the ethanol:water ratio is greater than 0.3:1 but having essentially no solubility in water or saliva at lower concentrations, and mixtures thereof.

11. An ingestible, nonfoaming, oral hygiene composition with a viscosity between about 30 and about 600 centipoises suitable for interrupting the formation of plaque consisting essentially of a mixture of alcohol, water, and from between about 0.05 and about 3.0 percent by weight of polyoxyethylene compounds having as a hydrophobe a polyoxybutylene polymer of at least 1200 molecular weight and mixtures thereof, and
   from between about 0.005 and about 0.3 percent by weight of a coating material insoluble in said polyoxyethylene compounds, selected from the group consisting of:
silicones,
silicone glycol copolymers,
polydimethyl siloxanes,
long chain hydrocarbons,
paraffins with several loci of branching and unsaturation,
carbowaxes,
polymers with a limited solubility in ethanol and water solutions where the ethanol:water ratio is greater than 0.3:1 but having essentially nob solubility in water or saliva at lower concentrations, and
mixtures thereof.

12. An article of manufacture containing an ingestible, nonfoaming dentifrice that coats mouth surfaces with a plaque matrix disrupting film spray consisting essentially of:
(a) a portable container fitted with a metered pump spray, containing:
(b) a sprayable liquid dentifrice comprising a combination of surfactant and coating substances wherein:
(c) the surfactant is selected from the group consisting of:
sodium lauryl sulfate,
sodium lauryl sarcosinate,
polyethylene glycol stearate,
polyethylene glycol monostearate,
coconut monoglyceride sulfates,
sodium alkyl sulfates,
sodium alkyl sulfoacetates,
block copolymers of polyoxyethylene and polyoxybutylene,
alkylpolyglycol ether carboxylates,
polyethylene derivatives of sorbitan esters,
propoxylates cetyl alcohol,
block copolymers comprising a cogeneric mixture of conjugated polyoxybutylene and polyoxylethylene compounds having as a hydrophobe a polyoxybutylene polymer of at least 1200 molecular weight,
a salt of a fatty acid, and
mixtures thereof, and
(d) the coating substance which is insoluble in said surfactant, is selected from the group consisting of:
silicones,
silicone glycol copolymers,
polydimethyl siloxanes,
long chain hydrocarbons,
normal paraffins having a chain length of 16 carbon atoms or greater,
paraffins with several loci of branching and unsaturation,
carbowaxes,
polymers with a limited solubility in ethanol and water solutions where the ethanol: water ratio is greater than 0.3:1 but have essentially no solubility in water or saliva at lower concentrations, and
mixtures thereof.

13. The article of manufacture according to claim 12 wherein the sprayable liquid dentifrice therein has a viscosity between about 30 and about 600 centipoises.

14. The article of manufacture according to claim 12 wherein the concentration of surfactant in the sprayable liquid dentrifice therein ranges from between about 0.05 and about 3.0 % by weight.

15. The article of manufacture according to claim 12 wherein the concentration of coating substance in the sprayable liquid dentrifice therein ranges from between about 0.005 and about 0.3 % by weight.

16. The article of manufacture according to claim 12 wherein the sprayable liquid dentrifice therein contains a humectant selected from the group consisting of glycerine, propylene glycol, sorbitol, xylitol and mixtures thereof.

17. The article of manufacture according to claim 12 wherein the portable container is clear, oriented polyethylene terephthalate.

18. An article of manufacture containing a dentrifrice spray comprising:
(a) a portable container fitted with a metered pump spray, said container containing:
(b) an ingestible, nonfoaming sprayable liquid dentifrice, with a viscosity between about 30 and about 600 centipoises, consisting essentially of a combination of ingestible surfactant and coating substances including;
(c) from between about 0.05 and about 3.0 percent by weight of a surfactant selected from the group consisting of:
sodium lauryl sarcosinate,
polyethylene glycol stearate,
polyethylene glycol monostearate,
coconut monoglyceride sulfonates,
sodium alkyl sulfates,
sodium alkyl sulfoacetates,
polyoxyethylene and polyoxybutylene block copolymers,
alkylpolyglycol ether carboxylates,
polyethylene derivatives of sorbitan esters,
propoxylated cetyl alcohol,
block copolymers comprising a cogeneric mixture of conjugated polyoxybutylene and polyoxylethylene compounds having as a hydrophobe a polyoxybutylene polymer of at least 1200 molecular weight,
a salt of a fatty acid, and
mixtures thereof, and
(d) from between about 0.005 and about 0.3 percent by weight of a coating material insoluble in said surfactant selected from the group consisting of:
silicones,
silicone glycol copolymers,
polydimethyl siloxanes,
long chain hydrocarbons,
paraffins with several loci of branching and unsaturation,
carbowaxes,
polymers with a limited solubility in ethanol and water solutions where the ethanol:water ratio is greater than 0.3:1 but having essentially no solubility in water or saliva at lower concentrations, and mixtures thereof.

19. A dentifrice spray according to claim 18 wherein the cleaning, coating composition contains a humectant selected from the group consisting of glycerine, propylene glycol, sorbitol, xylitol and mixtures thereof.

* * * * *